United States Patent [19]

Guha

[11] Patent Number: 5,373,452
[45] Date of Patent: Dec. 13, 1994

[54] INTANGIBLE SENSOR AND METHOD FOR MAKING SAME

[75] Inventor: Aloke Guha, Minneapolis, Minn.

[73] Assignee: Honeywell Inc., Minneapolis, Minn.

[21] Appl. No.: 683,505

[22] Filed: Apr. 15, 1991

Related U.S. Application Data

[63] Continuation of Ser. No. 560,506, Jul. 19, 1990, abandoned, which is a continuation of Ser. No. 240,888, Sep. 2, 1988, abandoned.

[51] Int. Cl.$^5$ .................. G01N 33/00; G06F 15/20
[52] U.S. Cl. .................. 364/550; 364/552; 364/556; 73/865.7; 395/22
[58] Field of Search .................. 395/22; 364/550, 552, 364/556, 551.01; 340/514, 515–517; 371/15, 17, 24, 25; 73/866.4, 432.1, 866, 865.7

[56] References Cited

U.S. PATENT DOCUMENTS

| | | | |
|---|---|---|---|
| 4,642,782 | 2/1987 | Kemper et al. | 364/550 |
| 4,644,480 | 2/1987 | Haruna et al. | 364/552 |
| 4,669,052 | 5/1987 | Bianco | 364/556 |
| 4,719,586 | 1/1988 | Moyer et al. | 364/552 |
| 4,773,028 | 9/1988 | Tallman | 364/550 |
| 4,807,162 | 2/1989 | Shibayama et al. | 364/552 |

OTHER PUBLICATIONS

R. P. Lippmann, "An Introduction to Computing with Neural Nets", IEEE ASSP Magazine, Apr. 1987, pp. 4–22.

D. E. Rumelhart, G. E. Hinton, and R. J. Williams, "Learning Internal Representations by Error Propagation", Parallel Distributed Processing—Explorations in the Microstructure of Cognition, vol. 1, MIT Press, 1987.

R. Hecht-Nielsen, "Applications of Counterpropagation Networks", Journal of the International Neural Networks Society, vol. 1, No. 2, 1988.

A. N. Kolmogorov, "On the Representation of Continuous Functions of Several Variables by Superposition of Continuous Functions of One Variable and Addition", Dokl. Akad. Nauk SSR, vol. 114, 1957, pp. 369–373; as cited in D. A. Sprecher, On the Structure of Continuous Functions of Several Variables, Transactions of American Mathematical Sciences 115, 340–355, Mar., 1965.

Specht, "Probabalisitc Neural Networks for Classification, Mapping, or Associative Memory", *IEEE Intl. Conf. Neural Networks* (1988) pp. 525–532.

Caulfield, "Applications of Neural Networks to the Manufacturing Environment", *Optical Testing and Metrology II* (1988), SPIE vol. 954, pp. 464–467.

Li et al. "Qualitative Analysis and Synthesis of a Class of Neural Networks", *IEEE Trans. on Circuits and Systems*, vol. 35, No. 8, Aug. 1988, pp. 976–986.

*Primary Examiner*—Michael Zanelli
*Attorney, Agent, or Firm*—Kenneth J. Johnson; Michael B. Atlass

[57] ABSTRACT

An intangible sensor for measuring intangible properties of a substance and a method for making the sensor is described. The intangible sensor may be embodied in a mapping neural network model. The intangible sensor herein is a device that quantitatively measures complex intangible properties of a sample of a substance. The term intangible implies a subjective connotation such as in the taste, creaminess or softness of a substance or product and therefore can only be subjectively defined. Although an intangible property is known to be a function of certain measurable physical properties of a substance, there are no known definitions of this function. The intangible sensor herein can implement this function simply without having any detailed knowledge of or making any analysis of the function.

9 Claims, 5 Drawing Sheets

| INPUT DATA | INTANGIBLE OUTPUT SCORES |
|---|---|
| (ALL INPUT VAR / PARAMETERS SUSPECTED TO INFLUENCE OUTPUT) | (AVERAGE HUMAN SCORE GIVEN TO INTANGIBLE PARAMETER) |

16

INTANGIBLE SENSOR AND METHOD FOR MAKING SAME

This application is a continuation of application Ser. No. 07/560,506, filed Jul. 19, 1990, now abandoned, which is a continuation of application Ser. No. 07/240,888, filed Sep. 2, 1988, now abandoned.

The invention herein relates to a sensor for measuring intangible properties of a substance and a method for making the sensor.

An intangible sensor embodying the invention herein and made in accordance with the method of the invention may be embodied in a mapping neural network model.

The intangible sensor herein is a device that quantitatively measures complex intangible properties of a sample of a substance. It is designed to be repeatable as well as non-specific and thus can be tailored to identify or detect specific intangible properties. The term intangible implies a subjective connotation such as in the taste, creaminess or softness of a substance or product and therefore can only be subjectively defined. Although an intangible property is known to be a function of certain measurable physical properties of a substance, there are no known definitions of this function. The intangible sensor herein can implement this function simply without having any detailed knowledge of or making any analysis of the function.

Advantages of the intangible sensor herein are:
i) It is used in conjunction with a set of standard, readily available sensors and thus no high-accuracy specific sensors have to be developed. The burden and difficulty of developing a specific sensor are thus avoided.
ii) There are no deterministic algorithms to be developed for relating every intangible property to a set of measurable properties. The intangible sensor learns by example just as humans do.
iii) Unlike a single physical sensor, the intangible sensor can be programmed or trained to different human preferences. For example, if an intangible sensor for taste is being developed, different versions can be developed by retraining the device to reflect different preferences while using the same set of standard input sensors.
iv) The intangible sensor herein is very robust in terms of its tolerance to noise in measurements. This is because a neural network computational model is used to capture the relationship between the intangible property and measurable physical properties of the substance under test. Neural network models are inherently fault-tolerant because they represent data in a distributed fashion.

A main object of the invention is to provide a new intangible sensor and a method for making said sensor.

Other objects and advantages of the invention will become apparent from the following specification, appended claims and the attached drawings.

Numbers in parentheses appearing hereinafter relate to references referred to at the end of the specification hereof.

DESCRIPTION OF INTANGIBLE SENSOR

Figure 1:
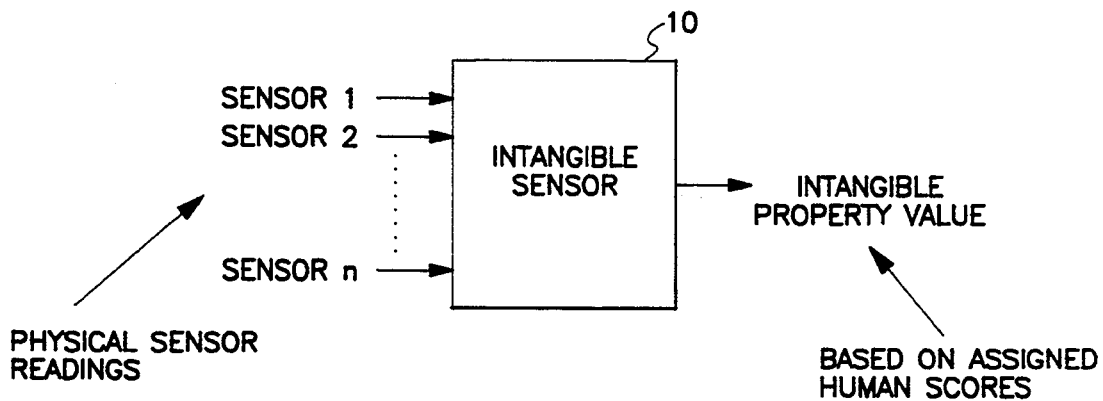
FIG. 1 is a schematic showing of the operation of an intangible sensor which embodies the invention disclosed herein.

The intangible sensor herein is based on a sensing scheme which implements the functional relation between measurable physical properties that determine the intangible property and human assigned scores that quantitatively describe the intangible property. FIG. 1 shows a schematic representation of the intangibles sensor 10.

The intangible sensor uses as inputs a number of measurements obtained through a set of simple sensors (marked 1 to n in FIG. 1). The set of sensors 1–n is chosen as a superset of sensors that measure physical properties suspected of influencing the intangible property. The intangible sensor as a device maps the physical input values to the human assigned scores of the intangible property for different samples of the product. Based on a multiplicity of "correct" responses provided by humans, the device 10 automatically develops the ability to produce an output score that approximates what a human would assign to the specimen being sensed or observed. In short, the intangible sensor imitates, and therefore can replace, the human monitor to evaluate the intangible property without establishing an exact physical definition.

COMPUTATIONAL MODEL FOR THE INTANGIBLE SENSOR

Figure 2:
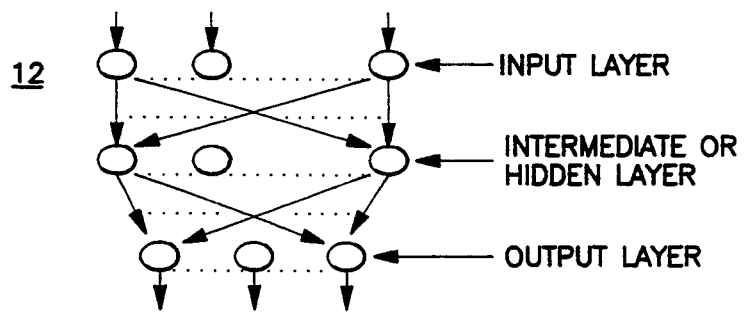
FIG. 2 illustrates a multilayer neural network for implementing the intangible sensor.

The computational model underlying the derivation of the functional relation is the mapping neural network 12 paradigm (1). In this model, a multilayer neural network is used to learn the relationship between the input sensor values of the physical properties of the substance and the human encoding (scores) of the intangible property. The multilayer neural network model used is usually a neural network employing a supervised learning algorithm (1). The preferred learning algorithm that is used is the back propagation learning algorithm or its variant (2). Other mapping neural network models such as the Kohonen associative model (3) and the counterpropagation model (4) can also be used. In case of the multilayer model, two to three layers (excluding the input layer where the inputs are fed into the network) must be used, that is, one or more hidden layers must be used as illustrated in FIG. 2. This is because, in order to realize any general function between real inputs and outputs, at least two layers must be used (2,5). FIG. 2 shows the typical neural network architecture required when employing the back propagation neural network to realize the mapping for the intangible sensor.

The multilayer network 12 approximates the general relationship between the measurable sensor values and the human sensory output. The large range of possible functions that can be realized by a feed-forward multilayer network can be shown by examining outputs 13 of each layer. The output 14 of any layer in the network can be analyzed by examining the functional behavior of an individual neural unit.

Figures 3, 4:
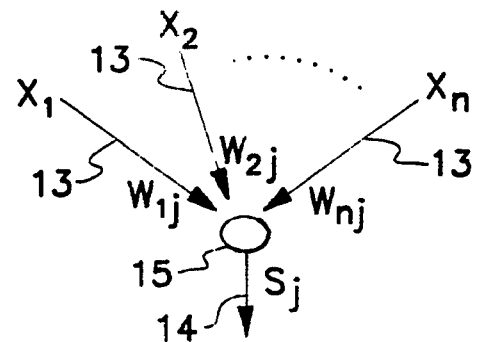
FIG. 3 illustrates a neural unit of the neural network of FIG. 2.
FIG. 4 illustrates a data training set for the neural network of FIG. 2.

FIG. 3 shows the inputs and the output of a single neural unit. The output 14 of unit $s_j$ is a function of the weighted sum of the inputs $x_1, x_2, \ldots, x_n$ or $$s_j = f\left(\sum_i x_i w_{ij} + t_j\right),$$

where $x_i$ is between 0 and 1, and $w_{ij}$ is a real number that specifies the strength of connection between input $x_i$ and $s_j$, and $t_j$ is a threshold term for the unit $s_j$, where i varies from 1 to n. The weights $w_{ij}$ are set after the neural network has been trained for mapping a specific input/output relationship. The most common function for f is the sigmoid function which can be described as follows:

$$f(x_1, x_2, \ldots, x_n) = 1/(1 + e^{\sum_i x_i w_{ij} + t_j})$$

As can be seen from the above function description, the output of f is always bounded. The outputs of the network are therefore always normalized between 0 and 1. Because the feedback network employs bounded neural units, it is guaranteed to be stable. This fact is important since it guarantees that the network can always be used to learn any arbitrary mapping withough exception.

The infinite range of mapping functions that can be learned by the network can be derived from the architecture of the feedforward network. If n input sensors are known to determine the single intangible output represented by the unit "o" in the following equation, these input sensor values are denoted by $s_1, \ldots, s_n$. If m units $x_1, \ldots, x_m$ are used in the hidden layer, then the two-layer network (excluding the layer of input variables) as shown in FIG. 2 realizes the relationships that can be expressed as:

$$o = f\left(\sum_j w_j \left(\sum_i f(w_{ij} s_i + t_i)\right) + t\right)$$

where $t_i$ and $t$ are the threshold terms for units in the hidden and output layers, respectively.

Kolmogorov (5) has shown that by using a layered network of real-valued functional units, any mapping can be accomplished by using a network containing two layers. Thus, if sigmoid units are used, a two-layered, or at worst, a three-layered network, would be sufficient to represent any arbitrary mapping. By using the back propagation learning algorithm (2), the different weights, $w_i$ and $w_{ij}$ (in case of a two-layered network) can be set to realize any arbitrary mapping required to relate the physical parameters to the intangible property. The weights are adapted iteratively until each input in the training set of samples yields the correct output taste score within acceptable tolerances.

DESIGNING AND IMPLEMENTATION OF THE INTANGIBLE SENSOR

The procedure followed in designing and implementing the intangible sensor 10 has three essential phases:

Phase I: Data Collection and Selection of sensors
Phase II: Training the Intangible Sensor
Phase III: Test and Validation In Phase I, all data available for different samples of the product, whose intangible property is to be sensed, is collected. This is the critical phase because the method of designing the sensor is completely data-dependent. In general, it is necessary that the samples collected have widely varying values of the intangible property. For example, if a sensor for taste for orange juice is being developed, then the sampling collected must have tastes varying from very good to very bad. Once the samples have been collected, a set of relevant sensors is identified. These sensors are those that can monitor measurable and tangible properties that are suspected of influencing the intangible property. For instance, if the taste of some juice is being measured, the sensors that would be considered in the set could include fructose or glucose sensors, a pH sensor for acidity, an alcohol sensor, a color sensor and density sensors. Each sample is then measured by these sensors (tangible data) as well as assessed by human evaluators (intangible data). The sensed and human score data for all samples constitute the training set 16 shown in FIG. 4 and used in Phase II.

Phase II uses the training set collected in Phase I and uses it to train the neural network 12 that is large enough relative to the size of the problem. Thus, if there are n input sensors and m components on which the humans evaluate the intangible property, the neural network 12 is defined with n inputs and m outputs. The back propagation algorithm (2) or an efficient variant is used to train the network the relationship between the sensed inputs and the intangible human scores.

After the training of the neural network 12 is completed (after the training converges), the test and validation is carried out in Phase III. The testing is done on samples that were not included in the training set and the output of the network model 12 is compared to the human-assigned score. If the network 12 compares favorably with the human scores for all test samples, then the neural network 12 is deemed to have learned the required relationship. Otherwise, two options are pursued. First, if the number of samples used are not sufficient for training, more samples are included (especially, the ones for which the network failed to give good results) in the training set. More data collection may then be required for testing. Second, the set of sensors used may not be suffient to capture the physical properties that influence the intangible property. In such a case, other suspected measurable properties of the substance must also be sensed. In case of either option, the three phases are repeated until the network model provides good prediction of the intangible property.

Figure 5:
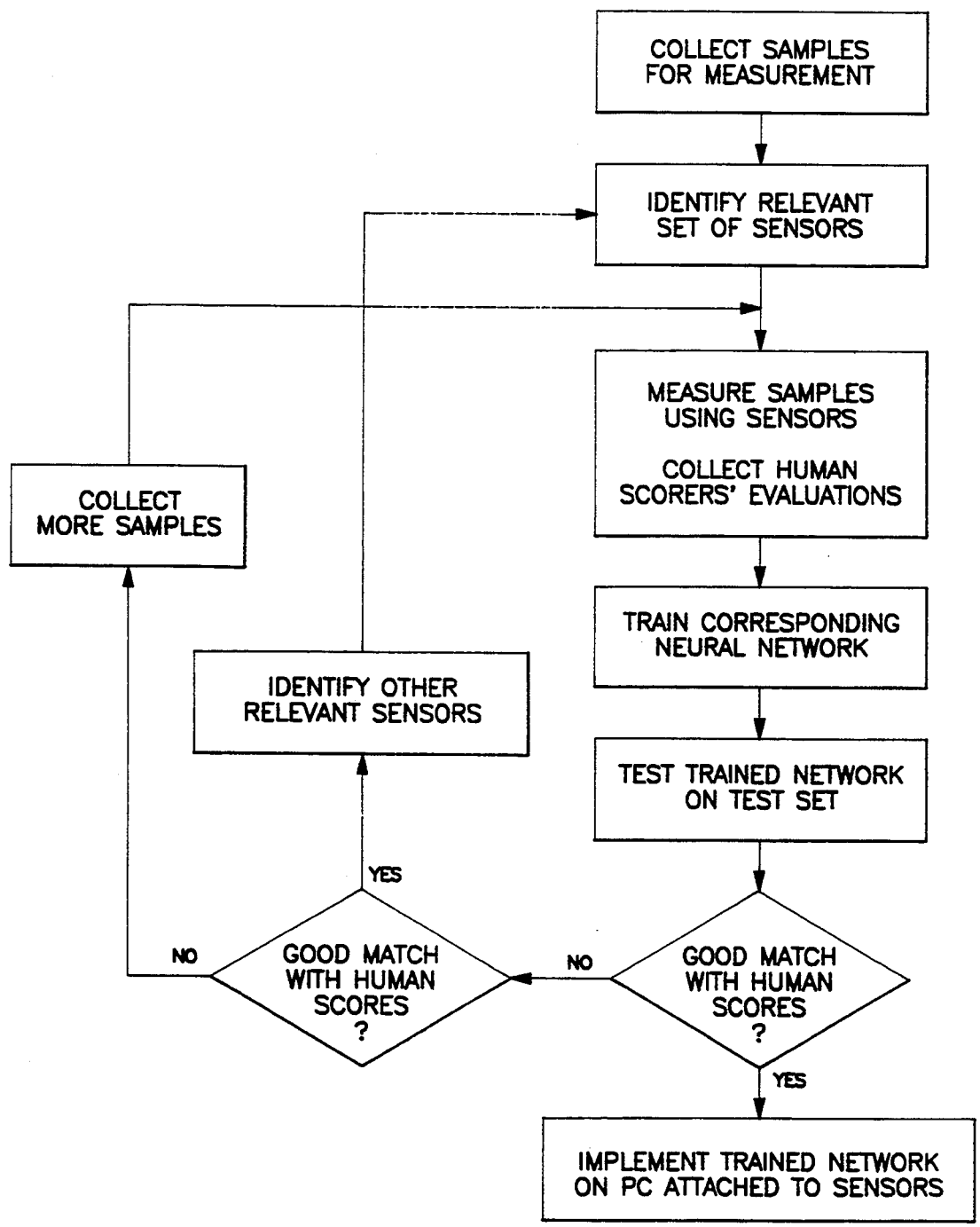
FIG. 5 is a flowchart for the design and implementation of the intangible sensor hereof.

The steps used in the design and implementation of the intangible sensor are depicted in the flowchart of FIG. 5.

EXAMPLES OF THE INTANGIBLE SENSOR

Two different domains of intangible properties of materials are chosen to demonstrate how the concept behind the invention can be used to design specific intangible sensors. The first intangible sensor is applicable to the domain of taste, specifically to taste fruit juices such as orange juice. The second sensor is applicable to characterizing solid food in the way humans do. It can be used to determine the chewiness of food, for instance cookies.

I. Intangible Sensor for Tasting Juice

Figures 6, 7:
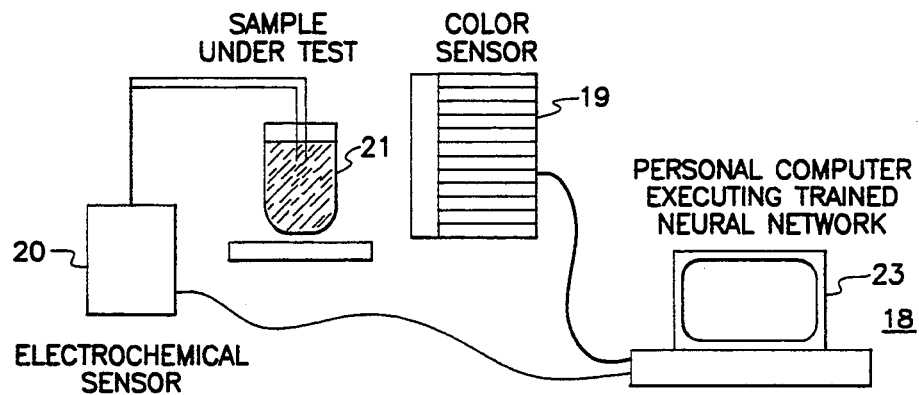
FIG. 6 is a schematic showing of a test setup of the invention herein for testing juices.
FIG. 7 is a chart showing a sample training set for an intangible sensor for tasting orange juice.

The intangible sensor 18 for tasting juice is shown in FIG. 6. Orange juice is chosen for illustrating this sensor. Here, two major physical (currently available) sensors are used. These are a twelve-channel Honeywell color sensor 19 and an electrochemical sensor 20 that provides the chemical signature of the juice sample 21. This minimal set of measurable physical inputs are expected to sufficiently characterize the taste of orange juice. For designing this sensor, the three phases previously outlined are followed.

Sample Data Collection: Two sorts of data are collected. Different orange juice samples that have a wide range of taste are collected. A taste panel tastes the different juice samples and scores them on either one (rating from good to bad) or many other (freshness, aroma, sweetness, etc.) attributes. The data possibly used in the training set 18 is shown in FIG. 7. Each sample is also measured physically for color and electrochemical signatures.

Training the sensor: A two-layered feedforward neural network 18 is set up to learn the mapping between the color and electrochemical inputs and the taste output/outputs. An iterative learning procedure, using back propagation, is used to establish the network weights and, therefore, the desired function to be realized by the neural network 18.

Testing the sensor: The trained network 18 is tested on samples not included in the training set. If the sensor scores are close, that is, within preset tolerance limits to the human scores, then the network has been trained well. After testing and validation is completed, the network 18 may be deployed in an operational mode. In the operational mode, the neural network model 18 is hosted on some computing platform, such as a personal computer 23 as shown in FIG. 6, and set up so as to predict taste scores when receiving data from the color and electrochemical sensors.

If the trained network did not score well, then more sample data is necessary to train the network. Training is complete only when the network has learned a sufficiently generalized mapping between the physical sensors and the human scores.

II. Intangible Sensor for Chewiness

Figure 8:
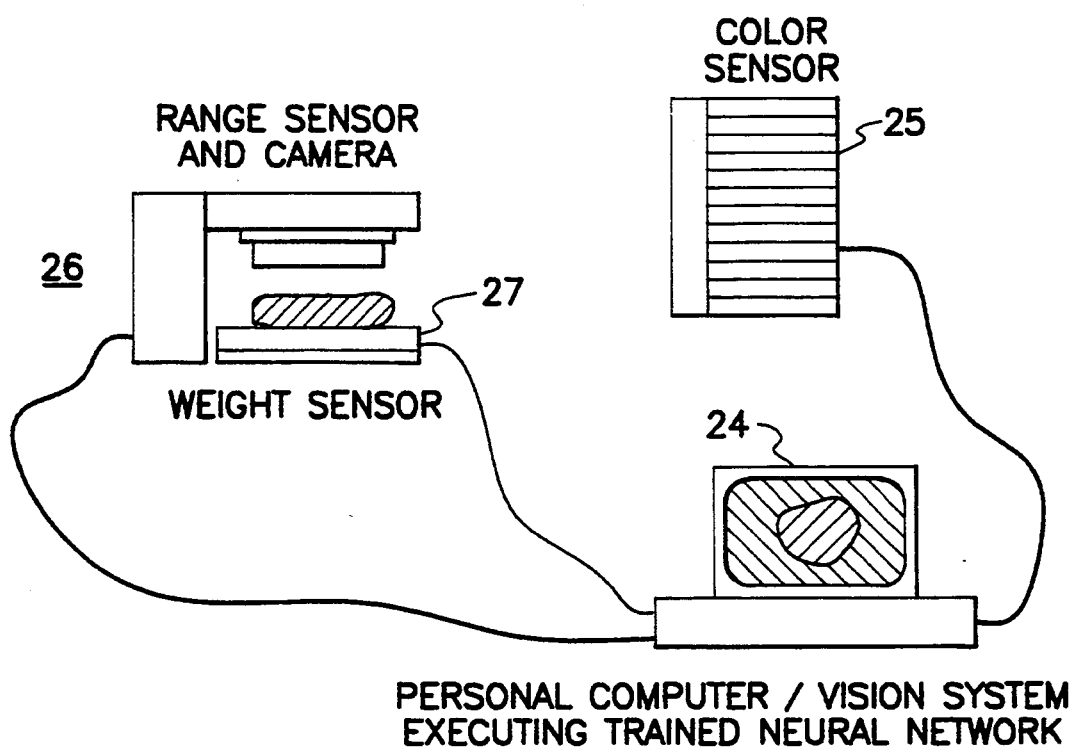
FIG. 8 is a schematic showing of a test setup of the invention herein for checking the chewiness of a solid food.

FIG. 8 shows an intangible sensor 24 for chewiness. The physical data that are measured in this sensor via sensor's 25, 26 and 27 are color, weight and dimensional measurements such as diameter and thickness. It is assumed that in the manufacturing of cookies in a batch process, a fixed weight of cookie dough is used. The network 24 is trained to map the physical data (average color (light brown to dark brown), thickness (how much rise in baked dough), weight after baking and the diameter of the cookie) to the intangible data of chewiness as determined by humans. The same three steps required in the previously described orange juice sensor are used to specify the neural network and the final intangible sensor.

DEFINITION

It is contemplated that the term "Physical Property" as used herein have a broad meaning in a general sense so as to mean any property of a substance, including any electrical, mechanical, chemical property, for which a physical measurement can be made by a single sensor of a known type. Thus, the term pH, for example, or if the degree of a reaction may be the parameter sensed, such are meant to be included.

REFERENCES

1. R. P. Lippmann, 'An Introduction to Computing with Neural Nets', IEEE ASSP Magazine, April 1987, pp. 4–22.
2. D. E. Rumelbart, G. E. Hinton, and R. J. Williams, 'Learning Internal Representations by Error Propagation', Parallel Distributed Processing—Explorations in the Microstructure of Cognition, Volume 1: Foundations. Editors: David E. Rumelhart, James L. McClelland, and the PDP Research Group. MIT Press, 1987.
3. T. Kohonen, 'Self-organization and Associative Memory', (second edition), Springer-Verlag: New York, 1988.
4. R. Hecht-Nielsen, 'Applications of Counterpropagation Networks', Journal of the International Neural Networks Society, Vol. 1, No. 2, 1988.
5. A. N. Kolmogorov, 'On the Representation of Continuous Functions of Several Variables by Superposition of Continuous Functions of One Variable and Addition', Dokl. Akad. Nauk SSR, Vol 114, 1957, pp. 369–373: as cited in D. A. Sprecher, "On the Structure of Continuous Functions of Several Variables", Transactions of American Mathematical Sciences 115, 340–355, March, 1965.

It is claimed:

1. A method for making an intangible sensor for measuring an intangible property of a particular substance, said method comprising the steps of:

(A) selecting a grading system for a human subjective evaluation of said intangible property which comprises a range of discrete index values;

(B) selecting at least two directly measurable tangible physical properties of said substance which affect said intangible property and selecting respective tangible sensors for measuring said physical properties;

(C)(1) establishing a relationship between said physical properties and one of said index values by selecting a sample of said substance and making relative thereto (1) physical measurements of said physical properties, and (2) subjective human evaluation of said intangible property comprising human selection of one of said index values corresponding to human sensation of said intangible property;

(C)(2) repeating step (C)(1) until a set of samples has been processed pursuant thereto which has said range of index values for said intangible property as defined in step (A);

(D) utilizing a mapping neural network model in a neural network having the capability to map a relationship between said measurable physical properties and said index values wherein said neural network adjusts internal weights such that inputs to said neural network which correspond to said tangible physical properties produce outputs from said neural network which correspond to said discrete index values in the same relation as exists in the set of samples processed in steps (C)(1) and (C)(2) above;

(E) mapping in said neural network for each of said samples via a supervised learning algorithm said physical measurements to a corresponding related one of said index values to thereby teach said mapping neural network model the relationship for said substance between said measurable physical properties thereof and said index values of said intangible property thereof.

2. The method according to claim 1 wherein said model is multilayered.

3. The method according to claim 2 wherein in order to realize a general function between real inputs and outputs said model has at least two layers including a hidden layer in addition to an input layer.

4. The method according to claim 1 wherein said model is a back propagation type.

5. A method for making an intangible sensor for measuring at least two intangible properties of a particular substance, said method comprising the steps of:

(A) selecting a corresponding number of grading systems for a human subjective evaluation of said intangible properties each of which comprises a range of discrete index values;

(B) selecting at least two directly measurable tangible physical properties of said substance which affect each of said intangible properties and selecting respective tangible sensors for measuring said physical properties;

(C)(1) establishing a relationship between said physical properties and one of said index values by selecting a sample of said substance and making relative thereto (1) physical measurements of said physical properties, and (2) subjective human evaluation of said intangible properties comprising human selection of one of said index values corresponding to human sensation of said intangible properties;

(C)(2) repeating step (C)(1) until a set of samples has been processed pursuant thereto which has said range of index values for said intangible properties as defined in step (A);

(D) utilizing a mapping neural network model in a neural network having the capability to map a relationship between said measurable physical properties and said index values wherein said neural network adjusts internal weights such that inputs to said neural network which correspond to said tangible physical properties produce outputs from said neural network which correspond to said discrete index values in substantially the same relation as exists in the set of samples processed in steps (C)(1) and (C)(2) above;

(E) respectively mapping in said neural network for each of said samples via a supervised learning algorithm said groups of physical measurements to corresponding related ones of said index values to thereby teach said mapping neural network model the relationship for said substance between said measurable physical properties thereof and said index values of the corresponding one of said intangible properties thereof.

6. The method according to claim 5 wherein said model is multi-layered.

7. The method according to claim 6 wherein in order to realize a general function between real inputs and outputs said model has at least two layers including a hidden layer in addition to an input layer.

8. The method according to claim 5 wherein said model is a back propagation type.

9. A sensor for identifying discrete values of an intangible property of a substance comprising:

a set of parallel input sensors for respectively measuring tangible physical properties of said substance, an output means for indicating degree of an intangible quality corresponding to a range of said discrete values chosen by subjective human evaluation of a sample set of said substance, and neural network means between said set of input sensors and said output means trained on subjective relationships between said discrete values and said measurements of said set of input sensors for determining said discrete values based on said measurements of said set of input sensors.

* * * * *